United States Patent [19]
Farah et al.

[11] 4,200,655
[45] Apr. 29, 1980

[54] BENZYL ALCOHOL VIRUCIDAL PROCESS

[75] Inventors: Alfred E. Farah, Schodack; William G. Gorman, East Greenbush, both of N.Y.

[73] Assignee: Sterling Drug Inc., New York, N.Y.

[21] Appl. No.: 933,792

[22] Filed: Aug. 15, 1978

[51] Int. Cl.$^2$ .......................................... A61K 31/045
[52] U.S. Cl. .................................................... 424/343
[58] Field of Search ......................................... 424/343

[56] References Cited
PUBLICATIONS

Physicians' Desk Reference, 27 ed., 1973, p. 655.
Chemical Abstracts 66: 44357p (1967).

Primary Examiner—Jerome D. Goldberg
Attorney, Agent, or Firm—Theodore C. Miller; B. Woodrow Wyatt

[57] ABSTRACT

The process of, and compositions for, neutralizing or destroying viruses with benzyl alcohol are disclosed.

5 Claims, No Drawings

BENZYL ALCOHOL VIRUCIDAL PROCESS

BACKGROUND OF THE INVENTION

1. Field of the Invention

This invention relates to a process and compositions for neutralizing or destroying a virus.

2. Description of the Prior Art

It has been shown (Hendley, Wenzel and Gwaltney, New England Journal of Medicine, vol. 288, pp. 1361–1364, 1973) that colds caused by rhinoviruses can be transmitted from person to person or from person to object to person by way of the hands. It is believed that self-infection takes place by transfer of virus from the fingers to the nasal mucosa or the conjunctiva. Similar transmittal of other types of virus is also believed possible. The resulting need for a topical virucidal substance and method of use and formulations thereof, especially for the hands, is satisfied by the present invention.

Benzyl alcohol is a well-known substance whose uses are mainly non-pharmaceutical. It has been used pharmaceutically as a "[t]opical antiseptic", and "local anesthetic" (The Merck Index, Eighth Edition, pp. 137–138) and as a "[p]harmaceutic aid (bacteriostatic)" (The Merck Index, Ninth Edition, Monograph 1138) and in veterinary medicine for relief of pruritis (both foregoing citations from The Merck Index), but is property as a virucidal substance has been heretofore unknown. The present invention reflects the discovery of this property.

SUMMARY OF THE INVENTION

In a process aspect the invention is the process of neutralizing or destroying a susceptible virus which comprises contacting the virus with a virucidally effective amount of benzyl alcohol.

In a composition aspect the invention is a composition for neutralizing or destroying a susceptible virus which consists essentially of a virucidally effective concentration of benzyl alcohol and a vehicle.

DETAILED DESCRIPTION OF THE INVENTION INCLUSIVE OF THE PREFERRED EMBODIMENTS

In Vitro Virucidal Activity of Benzyl Alcohol

The virucidal activity of benzyl alcohol against three strains of human rhinoviruses, herpes simplex viruses types 1 and 2 and two strains of influenza viruses is demonstrated by the following experiments.

Method: Rhinoviruses types 2, 14 and 17 were obtained from the National Institute of Allergy and Infectious Diseases and pools were prepared in a continuous cell line of human amnion cells (CATR). Herpes simplex viruses type 1 (Sheely strain) and type 2 (Curtis strain) were grown and pools were prepared in a monkey kidney cell line (BSC-1). Monolayers of three-day old CATR and BSC-1 cells grown in stationary tubes were used. Various concentrations of benzyl alcohol were prepared in a maintenance medium (M-199) and mixed with equal volumes of virus. Each mixture was incubated 10 minutes at room temperature followed by a ten-fold serial dilution from $10^{-1}$ through $10^{-7}$. Two-tenths ml. of each dilution was inoculated into tissue culture tubes, four tubes per dilution. Residual virus was allowed to adsorb for one hour, after which 0.8 ml. of maintenance medium (M-199+5% inactivated fetal calf serum) was added to each tube. Cultures were incubated at 33° C. for rhinoviruses or 37° C. for herpes simplex viruses and examined microscopically after 72 hours for the presence or absence of viral cytophatic effect. The virus control in each test consisted of simultaneous titrations of the virus from $10^{-1}$ through $10^{-7}$. To determine the cytotoxicity of benzyl alcohol to the assay system, a parallel set of cultures was treated in each test with identical concentrations of benzyl alcohol without virus. Only those levels of benzyl alcohol which had no cytotoxic effect were valid for virucidal interpretation. The absence of cytopathic effect in the monolayers was evidence of the virucidal effect. Virucidal activity was demonstrated when a three-log (99.9%) reduction or greater in virus titer was observed.

Influenza virus A2/Japan/170/62 (6th egg passage, allantonic fluid), influenza virus A/PR8/34 (5th egg passage, allantoic fluid) and ten-day-old embryonated chicken (White Leghorn) eggs were used in this study. In experiments with undiluted virus, 0.9 ml. of benzyl alcohol was mixed with 0.1 ml. of undiluted virus in allantoic fluid. The mixture was allowed to stand at ambient temperature for 10 minutes and was then rapidly diluted for ten-fold steps in phosphate-buffered saline to a final dilution of $10^{-8}$. In experiments with diluted virus, each virus pool was diluted to $10^{-3}$ in phosphate-buffered saline. This dilution was mixed with benzyl alcohol as described above and then diluted from $10^{-4}$ through $10^{-8}$. Two-tenths ml. of each final dilution was inoculated into the allantoic sac of each of five eggs. The eggs were incubated at 36.5° C. for 40 hours then chilled overnight at 4° c. One-half ml. of allantoic fluid was removed from each egg and mixed with 0.5 ml. of phosphate-buffered saline in tubes. One ml. of 0.75% washed chicken red blood cells was added to each tube. The tubes were shaken and allowed to stand at room temperature for 40 minutes. Hemagglutination patterns were read and the 50% egg infectious dose ($EID_{50}$) calculated for each level of benzyl alcohol by the method of Reed and Muench (American Journal of Hygiene, vol. 27, pp. 493–497, 1938). Appropriate toxicity controls were included.

Results: After ten-minute contacts of the seven viruses with benzyl alcohol titers of each of the viruses were reduced as follows:

| % Benzyl Alcohol | Virus | % Reduction |
| --- | --- | --- |
| 6 | Rhinovirus Type 2 | 99.99 |
| 2.5 | Rhinovirus Type 14 | >99.99 |
| 3 | Rhinovirus Type 17 | 99.99 |
| 3 | Herpes Simplex Type 1 | >99.99 |
| 3 | Herpes Simplex Type 2 | >99.99 |
| 6 | Influenza A2/Jap 170 * | complete |
| 6 | Influenza A/PR8 * | complete |
| 3 | Influenza A2/Jap 170 * | >99.99 |
| 3 | Influenza A/PR8 * | >99.9 |
| 1.5 | Influenza A2/Jap 170 * | none |
| 1.5 | Influenza A/PR8 * | none |
| 1.5 | Influenza A2/Jap 170 ** | >99.9 |
| 1.5 | Influenza A/PR8 ** | 99 |

* Undiluted
** Diluted 1:1000

The Compositions

The compositions of this invention are intended for topical virucidal use both in vitro and in vivo, especially for use on the hands and especially for preventing transmission of rhinoviruses. For these purposes the benzyl alcohol can be formulated in any appropriate vehicle, provided that the benzyl alcohol and the vehicle are compatible, that is, that the virucidal activity of the benzyl alcohol is not diminished by the vehicle. Thus, the compositions can be in the form of creams, foams, lotions, ointments, solutions or sprays. The vehicles can be aqueous or non-aqueous, for example alcoholic or oleaginous, or a mixture thereof and may additionally contain surfactants, emollients, lubricants, stabilizers, dyes, perfumes and preservatives. Conventional methods are used in preparing the compositions.

The foregoing compositions can be dispensed in premoistened pads or tissues. The latter can be packaged individually as described, for example, in U.S. Pat. No. 3,057,467 or multiply, in separate sheets as described, for example, in U.S. Pat. No. 3,836,044 or in a roll as described, for example, in U.S. Pat. No. 4,017,002.

EXAMPLE

The following example is a composition intended for use as a virucidal hand lotion wherein the vehicle is an aqueous surfactant-emollient mixture. The composition was prepared for in vitro virucidal testing with and without benzyl alcohol.

| Ingredient | Percent by Weight |
|---|---|
| Benzyl Alcohol | 6.00xxx |
| Glyceryl Stearate (and) PEG-100 Stearate | 3.00xxx |
| PEG-12-Buteth-16 | 2.00xxx |
| Myristyl Alcohol | 1.50xxx |
| Cetyl Alcohol | 1.50xxx |
| PEG-4 Laurate | 1.00xxx |
| PEG-4 Stearate | 0.500xx |
| Glycerin | 0.500xx |
| Perfume | 0.300xx |
| Carbomer-934P | 0.200xx |
| Dye | 0.00200 |
| Sodium hydroxide to adjust to pH 5.5, about | 0.0260x |
| Water to make | 100.00xxx |

In Vitro Virucidal Activity of the Composition

The virucidal activity of the composition of the foregoing example was determined against human rhinoviruses types 2, 14 and 17.

Method: Rhinoviruses types 2, 14 and 17 were obtained from the National Institute of Allergy and Infectious Diseases. Rhinoviruses types 14 and 17 were propagated in a continuous line of human amnion cells (CATR) and contained $\log_{10} 6.25$ $TCID_{50}$ and $\log_{10} 5.75$ $TCID_{50}$ per 0.2 ml. of virus, respectively. Rhinovirus type 2 was propagated in a continuous line of HeLa (Ohio) cells and contained $\log_{10} 6.5$ $TCID_{50}$ per 0.2 ml of virus. Rhinoviruses types 14 and 17 were titrated in monolayers of human amnion cells. Rhinovirus type 2 was titrated in HeLa cells. Virus assay: Two-tenths ml. of each dilution was inoculated in quadruplicate tubes and allowed to incubate for one hour. Eight-tenths ml. of maintanence medium (M-199+5% fetal calf serum) was added and cultures were incubated at 33° C. Each tube was examined for viral cytopathic effect at 72 and 96 hours.

Procedure for virus in activation:

Two-tenths ml. of each virus (undiluted infected tissue culture fluid) was mixed with 1.8 ml. of the composition of the foregoing example (except the perfume) or the vehicle alone (except the perfume). The mixture was homogenized for one minute on a vortex mixer and was then incubated for 10 minutes at room temperature. After incubation, 6 ml. of maintenance medium (M-109) was added to the composition mixture, which was centrifuged for 150 minutes at 40,000 rpm (159,000 x g). After centrifugation, the supernatant was removed, 2 ml. of maintenance medium (M-199) was added, and the pellet was resuspended with a vortex mixer and serially diluted to $10^{-6}$ in maintenance medium (M-199). As a control, 0.2 ml. of virus was diluted in 1.8 ml. of maintenance medium (M-199). The mixture was incubated for 10 minutes, 6 ml. of maintenance medium (M-199) was added and the mixture was centrifuged as described previously. For cytotoxic evaluation, to insure that the composition or vehicle above did not interfere with or obscure the virus assay system by causing the cells to detach or by some other mechanism, the composition examples and vehicle alone were mixed with 0.2 ml. of maintenance medium (M-199) rather than virus prior to dilution, centrifugation and assay.

Results: After ten-minute contacts of the three viruses with the composition, titers of each of the viruses were reduced by >99.99%. The vehicle alone had no significant effect on virus titers. Cytotoxicity of the composition and vehicle alone did not obscure observation of virucidal activity.

Negative Test Results

At 6% concentration benzyl alcohol was determined to be inactive against poliovirus type III and ECHO 9 and ECHO 11 viruses in vitro in tests similar to those described above for the rhinoviruses, herpes simplex viruses and influenza viruses.

We claim:

1. The process of neutralizing or destroying a rhinovirus or an influenza virus on a person which comprises topically applying to said virus a virucidally effective amount of benzyl alcohol.

2. The process according to claim 1 wherein a virucidally effective concentration of benzyl alcohol and a vehicle is applied to the virus.

3. The process according to claim 2 wherein the vehicle is an aqueous surfactant-emollient mixture.

4. The process of neutralizing or destroying a rhinovirus or an influenza virus in vitro which comprises topically applying to said virus a virucidally effective amount of benzyl alcohol.

5. The process according to claim 4 wherein a virucidally effective concentration of benzyl alcohol and a vehicle are applied to the virus.

* * * * *